United States Patent
Scherr

(10) Patent No.: US 6,696,077 B2
(45) Date of Patent: *Feb. 24, 2004

(54) SILVER ALGINATE FOAM COMPOSITIONS

(76) Inventor: George H. Scherr, 33 Monee Rd., Park Forest, IL (US) 60466

(*) Notice: Subject to any disclaimer, the term of this patent is extended or adjusted under 35 U.S.C. 154(b) by 0 days.

This patent is subject to a terminal disclaimer.

(21) Appl. No.: 09/912,337

(22) Filed: Jul. 26, 2001

(65) Prior Publication Data

US 2003/0021832 A1 Jan. 30, 2003

(51) Int. Cl.$^7$ .................. A61F 13/00; A16K 9/00; A61L 15/00
(52) U.S. Cl. .................. 424/443; 424/444; 424/445; 424/446; 424/447; 424/448
(58) Field of Search .................. 424/443, 444, 445, 446, 447, 448

(56) References Cited

U.S. PATENT DOCUMENTS

| 2,008,131 | A | * | 7/1935 | Dieck et al. ............ 424/443 |
| 2,396,514 | A | * | 3/1946 | Kreidl et al. ........... 424/404 |
| 2,459,896 | A | * | 1/1949 | Schwarz ................. 424/412 |
| 2,521,713 | A | * | 9/1950 | Goetz .................... 424/618 |

FOREIGN PATENT DOCUMENTS

EP         243096 A1  * 10/1987

* cited by examiner

Primary Examiner—Thurman K. Page
Assistant Examiner—Isis Ghali

(57) ABSTRACT

The invention described herein relates to the preparation of cellulosic foam products prepared from silver alginate and derivatives thereof and the process for preparing them. The silver alginate products and related silver products are amenable for use in the preparation of medical and veterinary dressings for the treatment of burns, wounds, ulcerated lesions, and related pathological states.

30 Claims, No Drawings

SILVER ALGINATE FOAM COMPOSITIONS

DESCRIPTION OF THE PRIOR ART

The effect of various metals on biological processes has generally been referred to as an "oligodynamic" action. A detailed discussion of the history of such oligodynamic action with particular emphasis on the use of silver is contained in Chapters 24 and 28 of the monograph by Lawrence and Block, *Disinfection, Sterilization, and Preservation*, Lea and Febiger, Philadelphia, 1968. Consequently, Chapters 24 and 28 of Lawrence and Block's treatise on disinfection are cited herein by reference in their entirety.

Goodman and Gilman (1943) reported that the toxic effects of silver compounds on microorganisms is probably due to the silver ions which precipitate the protein of bacterial protoplasm. It is very well known that soluble silver salts such as silver nitrate will quickly precipitate protein and oxidize to a dark brown or black precipitate. The silver protein complex so formed contributes to a sustained antiseptic action by slowly liberating small amounts of silver ions. Goodman and Gilman felt it probable that in the use of simple salts of silver as antiseptics, some metallic silver is obtained by reduction and that its oligodynamic action contributes to the anti-bacterial effect.

Studies examining the mechanism of action by silver in demonstrating antimicrobial activity led various workers to conclude that the surface area of silver ions was more important that the amount of silver nor the time that the substrate containing microbes was exposed to the silver. The silver was prepared in the form of a spongy metallic form or by coating various products which contain large surfaces such as sand. Thus Süpfle and Werner (1951) were able to show that *E. coli* placed in flasks having counts of 18,000 *E. coli* per ml of water. When such counts were exposed to flasks containing sand coated with silver at a concentration of 10% silver of the amount of sand, would result in a sterile environment in four hours. Even counts as high as 120,000 *E. coli* per ml of solution, resulted in sterility in 24 hours.

Clinical studies utilized a silver powder prepared by Rochat and Uzdins (1947) showed that particles of silver of a size of 2 microns to $\frac{1}{100}$ of a micron, when prepared in the form of a paste could be used to treat dental root canals, in the form of a spray to treat tonsillitis, or in the form of a powder in water suspension to treat abrasions and burns. Such silver compounds were successful for the treatment of severe burns, carbuncles and infected wounds. As such, the silver preparations promoted tissue granulation, suppressed fecal odors of wounds, accelerated healing, as well as prevented keloid formulation.

Kreidl and Kreidl (U.S. Pat. No. 2,396,514) prepared a cloth or gauze by treating the material with a solution of a silver compound, such as silver nitrate, followed by a soluble halide such as sodium chloride and after a period of time, which resulted in an insoluble silver chloride precipitate being impregnated into the cloth, they washed off the excess of silver chloride that was not absorbed onto the material, so resulting in an impregnated material which had antiseptic properties. The dressing containing silver chloride as prepared by Kreidl and Kreidl would have exerted minimal antimicrobial activity because, as is well-known in the profession, silver chloride is a highly insoluble chemical and is insoluble in water or other aqueous solutions to the extent of $0.000089^{10}$ parts per 100 ml of water.

Schwartz (U.S. Pat. No. 2,459,896) impregnated fibers such as nylon fibers with colloidal silver and then reduced the silver by treating the preparation with alkylamines. These fibers were then shown to have antimicrobial activity. Here also in the Schwartz patent nylon fibers which are not soluble in aqueous solutions or tissue exudate, would be expected to have very low antimicrobial activity, because the only colloidal silver that would be available to act on microorganisms are those colloidal silver particles on the very surface of the nylon fiber and they would essentially be few and far between and fixed in situ of the nylon. In addition, such a preparation of a colloidal silver-impregnated nylon fiber would not have the characteristics that have been shown to be important in utilizing silver as an antimicrobial agent, in that the total silver surface area of silver ions available to the tissue exudate would be minimal, because colloidal silver is silver in the non-ionic state.

In a subsequent patent (U.S. Pat. No. 2,459,897) Schwartz also produced fibers that were impregnated with silver and reducing agents of silver in which the reduction of the silver was achieved with heterocyclic secondary amines such as piperidine or pyrrolidine. These fibers thereby developed antimicrobial activity. In this patent of Schwartz (U.S. Pat. No. 2,459,897), Schwartz recognized the necessity to reduce the free silver to silver ions and thereby incorporated secondary amines which acted as reducing agents which were also impregnated into the nylon fibers in order to procure antimicrobial activity. Here also, however, the only antimicrobial activity that would be available to a tissue exudate would be those on the very surface of the fiber and all of the reduced silver ions present inside the nylon fiber would not be available to the tissue exudate, therefore, the antimicrobial activity would be diminished.

Goetz, in his U.S. Pat. No. 2,521,713 formed silver complexes which were antimicrobial by utilizing a finely divided silver oxide sludge and finely divided zinc oxide to react for a short period of time. The mixture was then dried and made into granules or pellets. These complexes in the form of a paste could be used as germicides for the treatment of burns, wounds, or skin infections. In this patent by Goetz, the silver oxide sludge so prepared would be expected to have minimal antimicrobial activity, because silver oxide in the form of $Ag_2O$ is soluble in aqueous solutions (and therefore tissue exudates) to the extent of $0.0013^{20}$ parts per hundred. The oxide of silver as silver oxide $Ag_2O$ is essentially considered insoluble in water. Because of the highly insoluble nature of the silver oxides, ionization of the silver oxides would be minimal and therefore antimicrobial activity also would be significantly diminished.

In a patent by Wilhelm Dieck and Sally Schiff (U.S. Pat. No. 2,008,131) the inventors relied exclusively on oxides of silver to procure antimicrobial activity. Thus even when a solution of silver permanganate utilized by the inventors was reduced, the inventors indicate the possible production of a silver oxide-manganite compound, which compound may (emphasis added) be a silver manganite compound having the composition of $Ag_2O_2MnO_2$.

Consequently, the remarks we have made above stipulating the high degree of insolubility of the silver oxide compounds are germane to the Dieck & Schiff patent. Further, even if the hypothetical compound, such as the silver manganite formula postulated by the authors was correct, there are no experiments cited to determine whether any antimicrobial activity is due to the highly insoluble silver oxides or to the presumed manganese oxide which the authors set forth in a number of the claims of their invention.

In the patent by Conconi (U.S. Pat. No. 2,283,883) the inventor claims that pure silver, when impregnated into a clay or related porous candle, will act as a filter to inactivate microorganisms present in solutions that are passed through such a filter. The invention of Conconi claims that the oligodynamic effect is highest when the metallic agent consists of pure silver. However, Conconi prepares his presumable silver clay matrix in the form of a candle by starting with silver nitrate and then reducing the silver nitrate with reducing agents to form metallic silver. Nowhere in Conconi's invention is it shown that 100% of the silver nitrate has been so reduced to metallic silver since even very dilute solutions of silver nitrate are well known in the profession to be highly antimicrobial in their activity and even trace amounts of silver nitrate that have not been reduced would show very marked antimicrobial activity. In any event, the patent of Conconi in all of the claims relies exclusively on pure silver in the form of a silver ceramic or clay candle to act as an antibacterial agent for solutions that would be passed through such a candle.

REFERENCES CITED

The present specification refers to the following publications all of which are incorporated herein by reference.

Goodman, L. and Gilman, A., 1065 *The Pharmacological Basis of Therapeutics*, 3$^{rd}$ Ed. New York, The Macmillan Company.

Lawrence, C. A. and Black, S. S., Disinfection, Sterilization and Preservation, Lea and Febiger, Phil., 1968, Chapters 24 and 28.

Rochat, C. and Uzdins, K., 1947 Katadyn (silver preparation): clinical application. Schweiz med. Wochschr., 77, 1100–1104.

Süpfle, K. and Werner, R., 1951 Microdeosimetric investigation of the oligodynamic effect of silver. Mikrochemie ver Mikrochim. Acta., 36/47, 866–881.

ATTRIBUTES OF THE INVENTION DESCRIBED HEREIN

The rationale I have discovered in preparing a silver alginate molecule as an antimicrobial agent for use in dressing has to do with the fact that soluble silver salts, such as silver nitrate, react with alginates, such as sodium alginate to form an aqueous-insoluble silver alginate moiety. The silver alginate will slowly soften in tissue exudate and gradually begin to dissolve, slowly releasing silver ions. In addition, a small amount of colloidal silver present in the dressing has the advantage of being molecular silver, whose gradual reduction over an extended period of time will release silver ions which have excellent oligodynamic activity.

In addition to the silver alginate as a component of the medical dressing which I have designed, an additional amount of calcium alginate may be present in the dressing as well as colloidal silver. Both have attributes which enhance the efficacy of the antimicrobial activity of the dressing. Thus, I find that an amount of calcium alginate present together with the silver alginate in the dressing acts to retain the integrity of the gel structure of the dressing that is to be applied to a wound or burn when the silver alginate begins to release silver ions, thereby softening the matrix in which the silver alginate is contained if calcium alginate were not present, This is due to the fact that calcium alginate forms a more stable and stronger molecular structure that silver alginate due to the very strong binding between the calcium ions and the alginate molecule. A concentration as little as one part in 100,000 of sodium alginate in aqueous solution can result in precipitation of calcium alginate in the presence of such calcium salts as calcium chloride. Consequently the use of silver alginate in a matrix of calcium alginate retains a stronger integrity of the dressing when applied to a wound over an extended period of time.

There are polymers other than calcium alginate, which can form a high viscosity matrix to be mixed with the silver alginate. Such polymers include Sodium Carboxymethylcellulose, Xanthan Gum, Hyaluronic Acid, Polylactic Acids, Pectin, Natural Gums, (like Acacia, Agaragar, Karaya, Tragacanth, Locust, Guar, Xanthan, Gelan Gum), Cellulose Gums (like Carboxymethylcellulose, Methylcellulose, Hydroxypropyl, Hydroxyethylcellulose) etc.

The release of silver ions from the silver alginate acts to immediately provide an oligodynamic antimicrobial action. The presence of colloidal silver, which will slowly reduce over an extended period of time, will act to prolong the antimicrobial activity of the silver ions, because of the gradual reduction of the colloidal silver to silver ions. It is well accepted that colloidal preparations of silver are actually very finely divided particles of silver, which are so small that they appear to go into solution, but are actually permanent suspensions of insoluble silver.

My composition of silver alginate to be incorporated into medical or veterinary dressings for the treatment of wounds or burns, acquires an additional attribute which is desirable in maintaining the antimicrobial activity of silver in a medical dressing as opposed to other silver compounds currently in use. Thus for example, silver sulphadiazine has been used as a component for medical dressings for use in the treatment of wounds, lesions, ulcers, and burns and this compound is a complex in which silver has been covalently linked to the sulfonamide, sulphadiazine (U.S. Pat. Nos. 6,153,215; 5,989,535). The mechanism of action of the sulfonamides stems from the fact that they are essential metabolic inhibitors of para-aminobenzoic acid (PABA). The antimicrobial action of the sulfonamides is due to the circumstance that PABA, which is part of the folic acid molecule, is essential to many microorganisms, but is not essential to mammalian cells. Mammals do not have to synthesize folic acid, but absorb it from their diet. The related sulfonamides to the sulphadiazine in silver sulphadiazine such as sulfamerazine, sulphanilamid, and many others, requires that a sulfonamide that will act as an antagonist to PABA must have a primary aromatic amino group and this amino group must not be substituted unless by a group which is readily broken down in the body. This means that microorganisms that become resistant to sulphadiazine will also be resistant to a wide series of other sulfonamides that have the primary aromatic amino group. Because of the possible risk in establishing a family of resistant organisms that otherwise would be susceptible to sulfonamides, I have chosen to covalently link the silver molecule to alginate which has no nitrogen and is essentially innocuous as a sensitizing agent or as a potential to result in the selection of microorganisms resistant to sulfonamides that otherwise would remain susceptible.

The use of various dressings frequently require that they be very soft and amendable to being draped around fingers, arm, or legs where injury has occurred. Consequently, it is a desirable attribute of such dressings to be highly flexible and amenable to being easily draped without their surface being distorted by the stress of such draping. It has been discovered that the addition of a compound such as sodium tetraborate (borax) results in the silver alginate foam composition to become highly flexible, have an increased elasticity, and can be readily draped around small circumferences such as a finger without distortion or breakage of the alginate dressing so formed.

Since the silver alginate foam composition prepared herein is highly viscous and would result in a viscosity that may be difficult to layer in a homogeneous thin layer on a plate to permit its drying, it was discovered that the addition of ammonia in aqueous solution or ammonium salts would reduce the viscosity of the silver alginate foam composition and significantly improve the ease with which the layering of the silver alginate foam composition may be layered. Since, during the drying process, free ammonia is liberated from such a composition, which has included the use of a solution of ammonia, liberation of the ammonia will then result in enhanced viscosity and concomitantly increase strengthening of the foam composition thus prepared by the removal of ammonia during the drying process.

Having set forth the tenets of the invention contained herein the following non-limiting examples illustrate various compositions that are inherent in our invention.

DESCRIPTION OF THE PREFERRED EMBODIMENTS

EXAMPLE 1

Place 750 ml of deionized water into a plastic container and, with stirring, slowly add 35 grams of Kelco HV brand of sodium alginate. The stirring should be sufficiently vigorous to form a vortex in the water so that the sodium alginate added to the water is directed into the middle of the vortex to ensure a very efficient dispersion of the alginate particles and so increase the speed of solution. The mixture is stirred until all of the sodium alginate has been dissolved.

To the sodium alginate solution prepared as above, add:
75 ml of a 10% solution of silver nitrate ($AgNO_3$) with continuous stirring.

After 15 minutes of continuous stirring, remove a 5 ml aliquot from the silver alginate slurry, and add 5 ml of a 3% solution of sodium chloride. The lack of any silver chloride white precipitate will indicate that all of the silver nitrate has reacted with the sodium alginate. If this test indicates that there is still residual silver nitrate present, merely add 10 gm quantities of the sodium alginate to react with any excess silver nitrate that might remain unreactive.

It is desired that the amount of silver nitrate added to the sodium alginate be less than the stoichiometrically required amount to react completely with all of the sodium alginate thus leaving some unreactive sodium alginate in the mixture.

With the silver alginate slurry continuously being stirred, add 20 ml of the surface active agent polyoxyethylene-polyoxypropylene block polymer (L64, Wyandotte Corp.), and 6.9 ml of the surface active agent polyoxethylenesorbitan monooleate (Tween 80®, Atlas Chemical Industries, Inc.,).

After stirring vigorously for approximately ten minutes to ensure that all of the ingredients have been dispersed, add 15 grams of sodium bicarbonate ($NaHCO_3$) followed by 30 ml of a dilute solution of acetic acid prepared by diluting one part of glacial acetic acid with two parts of deionized water.

The diluted acetic acid should be added very slowly with a pipette, again into the vortex of the stirred mixture, and vigorous stirring continued for approximately five minutes.

Following the addition of the acetic acid, the composition will gradually become more viscous.

The range of the desirable pH of the final composition should be between 6.8 and 7.5. Should adjustment of the pH become necessary, such adjustment can be made either with 1 N of acetic acid or a solution of 1.5 N sodium bicarbonate.

The alginate composition thus prepared will contain a considerable amount of foam, which foam will not rise to the surface of the alginate composition, because the viscosity of the final composition is sufficiently high to overcome the buoyancy of the foam.

When poured onto a plate, such as one made of plastic or metal, the dish may be air-dried or placed into a drying oven on the following schedule of drying:

70° C.—2 hours

60° C.—2 hours

40° C.—until dry

Alternatively, the alginate composition prepared as above can be poured onto a backing composed of a cotton-rayon mixture or a polyester non-woven backing, so that an amount of the alginate foam mixture penetrates in to the fiber and thus when dry, will retain this backing as part of the dried finished dressing.

The U.S. Pat. No. 5,674,524 expressed novelty in that prior to said U.S. Patent, the manufacturers of alginate fiber dressings were obliged to recommend that, once the alginate fiber dressing is placed on a wound, then a secondary sterile dressing would have to be affixed on top of the alginate dressing prior to its being affixed in place with adhesive tapes. The U.S. Pat. No. 5,674,524 resolved the laborious and expensive procedure for alginate dressings to require two separate sterile dressings to be affixed over a wound. This was resolved by utilization of needle punching of the alginate fiber dressing to a backing following the carding operation. It is a unique attribute of the patent described herein, that even needle punching is unnecessary to have the foam silver alginate composition affixed to a suitable backing of an alginate dressing.

It is thus another salient advantage of the patent described herein that the dried silver alginate foam composition, when ready to be cut in to appropriate sized dressings, packaged, and sterilized ready for use, already has a backing affixed to it and does not require any additional secondary sterile backing after the silver alginate composition is placed on an open wound.

EXAMPLE 2

Prepare all of the ingredients as described in Example 1 up to and including the addition of the L64 and Tween 80. With continuous stirring, add 30 ml of a 10% solution of calcium chloride ($CaCl_2.2H_2O$). The calcium chloride will react with any unreacted sodium alginate forming aqueous insoluble calcium alginate.

Add 15 grams of sodium tetraborate ($Na_2B_4O_7.10H_2O$) dissolved in 150 ml of water. With continuous stirring, add 110 ml of glycerin and 33 ml of ammonium hydroxide (28% $NH_3$).

Add 15 grams of sodium bicarbonate ($NaHCO_3$) followed by 30 ml of a dilute solution of acetic acid prepared by diluting one part of glacial acetic acid with two parts of deionized water.

The diluted acetic acid should be added very slowly with a pipette, again into the vortex of the stirred mixture, and vigorous stirring continued for approximately five minutes.

Following the addition of the acetic acid, the composition will gradually become more viscous.

The alginate composition thus prepared will contain a considerable amount of foam, which foam will not rise to the surface of the alginate composition, because the viscosity of the final alginate composition is sufficiently high to overcome the buoyance of the foam.

The silver alginate-calcium alginate composition thus prepared can be poured into a plate or onto a suitable backing and dried as described in Example 1 above.

In order to determine the antibiotic activity of the silver alginate composition prepared as above, and to compare such antibiotic activity to silver sulphadiazine, two sterile plastic Petri dishes were poured aseptically with Tryptic soy agar and the surface inoculated with *E. coli* B/r to result in confluent growth. A 5 mg sample of the silver alginate-calcium alginate composition procured after drying, was placed in the center of one of the plates and a 5 mg quantity of silver sulphadiazine placed in the other.

After incubation at 35° C. for 48 hours the diameters of the zones of inhibition for the silver alginate composition and the silver sulphadiazine preparation, respectively, were 15.0 mm and 6.0 mm.

EXAMPLE 3

The zinc salt of bacitracin, having a concentration of 67 IU/mg, is added in an amount of 230 mg to 10 ml of deionized water. Neomycin sulphate powder assaying as 704 mcg neomycin/mg of antibiotic is added to 10 ml of deionized water in an amount of 135 mg. Polymyzin B sulphate containing 8547 units of polymyxin B/mg of powder is added to 10 ml of deionized water in an amount of 22.6 mg. The three separate solutions are stirred until all of the antibiotics have been dissolved.

The antibiotic mixture thus prepared is added to the preparation of Example 2 following the addition of the 30 ml of a 10% solution of calcium chloride. The antibiotic solutions and the silver alginate-calcium alginate composition are then stirred until they are homogeneously mixed together and the composition can then be poured onto a plate surface or poured onto suitable backing and dried as described in Example 1 above.

EXAMPLE 4

A 750 ml quantity of 4.6% aqueous solution of sodium alginate as prepared above in Example 1 is added to a 4 liter container. To the sodium alginate solution prepared as above, add 75 ml of a 10% solution of silver nitrate ($AgNO_3$) with continuous stirring. To the silver alginate preparation thus prepared add the following ingredients in the following order:

60 ml of glycerin 200 ml of deionized water 6 ml of Tween 80

6 ml of L64 surface active agent 15 grams of sodium bicarbonate 7.5 grams of ammonium alginate (as sold under the trade name of Superloid® manufactured by Kelco Corporation).

With continued and vigorous stirring, add 1.0 gram of calcium sulphate, and 50 grams of maltodextrin with a dextrose equivalent of 13.0 to 17.0 as prepared by Aldrich Chemical Company, Inc.

The ingredients are stirred vigorously with a stirrer until the composition becomes viscous and to this composition is added 20 ml of ammonium hydroxide and 250 ml of deionized water.

Dilute acetic acid prepared as described above in Example 1, is slowly added with a pipette to a total amount of 11.0 ml.

The dilute acetic acid will react with the sodium bicarbonate and form a foam which remains intact in the semi-solid composition, which can be continuously stirred until it is ready to pour onto the surface of a plate or backing where it can be dried at room temperature, or in an oven as described in Example 1.

The pH may be adjusted as indicated above in Example 1.

Alternatively, the composition can be layered onto a gauze, cotton, or polyester backing where, when dry, it will adhere to and become affixed to the fibers of the backing. The dried finished dressing can be cut, packaged into suitable packages as is well known in the profession and sterilized and stored in hospital settings to be used when required.

The silver alginate-calcium alginate foam composition when in contact with an open wound will gradually become hydrocolloidal, will permit the continuous diffusion of the silver ions as well as the maltodextrin to the site of the wound, and will retain all of the clinical advantages that are delineated in U.S. Pat. Nos. 5,177,065 and 4,778,679 for maltodextrin.

EXAMPLE 5

All of the ingredients that are described in Example 4 above are prepared in the same way and to the semi-solid composition with stirring is added 0.5 gm of ascorbic acid.

After stirring to ensure homogeneity of all of the ingredients, the silver alginate-calcium alginate composition can be poured onto the surface of a plate or a backing where it can be dried at room temperature or in an oven as described in Example 1 above.

EXAMPLE 6

The silver alginate-calcium alginate composition, as described in Example 1, is prepared with stirring and to this composition is added a dispersion of 100 ml of bovine collagen containing 200 mg/ml of bovine collagen.

The entire composition, after appropriate stirring, can now be layered onto the surface of a plate or suitable backing where it can be dried at room temperature or in an oven as described in Example 1 above.

EXAMPLE 7

Colloidal silver is prepared utilizing a silver colloid generator as is well known in the profession. It is preferred that a 750 ml volume of deionized or distilled water be prepared containing a 10 parts per million (ppm) of colloidal silver. Such a solution of colloidal silver in deionized water can therefore be utilized as the base for dissolving 35 gm of sodium alginate and all of the other ingredients as described in any of the Examples 1–6 above.

EXAMPLE 8

The composition as described in Example 4 above is prepared following which and with continuous stirring is added one gram of a highly hydrophilic preparation called "Drimop"® as manufactured by Multisorb Technologies which is a sodium polyacrylate polymer.

The sodium polyacrylate polymer is highly hydrophilic and therefore, an amount of water would be retained by this product, even after drying in accord with the process set forth in Example 1. The unique value of adding a small amount of a highly hydrophilic preparation results in the retention of bound water to such a hydrophilic agent as the sodium polyacrylate polymer which thus results in a dressing having an amount of moisture which retains a 'cool' touch when the dressing is applied to an open wound. The "Drimop," sodium polyacrylate polymer being highly hydrophilic, also enhances the moisture-absorbing capacity of the dressing when it is applied to an open and/or exudating wound.

The silver alginate composition thus prepared may be spread on a flat surface and/or onto a suitable backing as described in Example 1 above and air or oven-dried, again as described in Example 1 above.

The above descriptions and examples illustrate particular constructions including the preferred embodiments of the solutions. However, the invention is not limited to the precise constructions described herein, but, rather, all modifications and improvements thereof encompassed within the scope of the invention.

The sodium alginate principally utilized in the examples described herein was one having an aqueous viscosity of 753 cP at 1.25% concentrations. It is clear that other sodium alginates having other viscosities may be utilized without deviating from the novelty of the revelations contained in this patent as long as the alginate is of a concentration and viscosity that can be reasonably poured into a mold when a calcium or other anion alginate precipitating molecule is added to the sodium alginate.

The soluble silver salt utilized in the examples cited above for precipitating the compound of silver alginate, was silver nitrate. It is clear that other aqueous soluble silver salts may be utilized to precipitate silver alginate without deviating from the novelty of the invention described herein.

Although the alginate used in the examples described herein was sodium alginate, it is clear that other water-soluble alginates may be utilized without deviating from the novelty of the invention described herein, such as water soluble ammonium alginate, magnesium alginate, or potassium alginate.

The concentration of colloidal silver described in the examples above, was 10 ppm. It is clear that other concentrations of colloidal silver might be utilized without deviating from the novelty of the invention described herein. Thus, for example, should one desire to prepare a dressing containing silver alginate and colloidal silver ions, in which the colloidal silver concentration is greater than 10 ppm in order to extend the period of time that the dressing would be effective in releasing silver ions, then such enhanced concentration of colloidal silver would be readily feasible.

It is well known in the profession that various glycols will act as plasticizers and may be used to improve the flexibility of alginate films or fibers. The plasticizer that we have principally used in the examples described herein has been glycerin because of its low cost and ready availability. It is clear however, that other plasticizers may be utilized such as propylene glycol or ethylene glycol without deviating from the novelty of the invention described herein.

In the examples cited herein, calcium chloride and calcium sulphate have been utilized to provide the calcium ion which precipitates the insoluble calcium alginate which serves to entrap into the calcium alginate matrix other components as described herein. It is clear, as has been mentioned, that other salts may be utilized to precipitate the alginate such as those of aluminum, zinc, copper, or chromium, and these insoluble alginates may readily be utilized to precipitate the coercive alginate mixture described in the Examples provided herein without deviating from the essential merits of this invention. However, since the alginate compositions are to be utilized in and on biological tissues, the particular salt utilized to precipitate the alginate should be dictated by any restraints of toxicity or other untoward reactions that might result from their use for the preparation of bandages, dressings, or surgical products.

Note that in Example 6, we utilized bovine collagen as a component in the alginate mixture so that the insoluble silver alginate-calcium alginate foam gel will contain an agent which has haemostatic activity, and therefore, would serve to stem the flow of blood from a wound when a dressing containing collagen is placed thereon. However, it is clear that other collagens such as porcine collagen may be incorporated into the dressings described herein without deviating from the essential merits of this invention.

Note that in Example 3 we incorporate antibiotics into the alginate composition. Other medicaments and/or drugs that may be delivered by means of this invention, but are not limited to this invention include:

Analgesics narcotic and non-narcotic (e.g. Morphine, Hydromorphine, Pentazocine, APAP)

Anti-inflammatory drugs steroidal (e.g. Hydrocortisone)

Anti-inflammatory drugs, non-steroidal (e.g. Pioroxicam, Naproxen, Diclofenac, Ketoprofen, Ibuprofen)

Anti-acne products (e.g. Salicylic Acid, Retinoic Acid, Azelaic Acid)

Local anesthetics (e.g. Lidocaine, Pramoxine, Benzocaine)

Steroids (e.g. Testosterone, Estradiol, Progesterone and its conjugates)

Antiperspirants (e.g. Zinc Salts, Aluminum and Zirconium complexes)

Dermatologicals (e.g. Antifungals, Antibiotics, Retinoids, alpha-Hydroxy Acids, Moisturizers)

Burn preparations (e.g. Lidocaine, Pramoxine, Diphenhydramine, Nidocromil, Cromoglycate)

Antifungal (e.g. Miconazole, Econazole, Terconazole)

Antiviral (e.g. Acyclovir, Behenyl Alcohol)

Hair growth stimulants (e.g. Monoxidil, Finasteride, Dexpenthenol, alpha-Hydroxy Acids)

Histamine blockers (e.g. Diphenhydramine Hydrochloride, Loratadine, Terfenadine)

Moisturizers (e.g. Water, Glycerin, Petrolatum, Dimethicon, Lactic Acid Salts, alpha-Hydroxy Acids).

Many of the examples described herein utilize the surface active agents such as those characterized as Tween 80 or Pluronic L64. These surface-active agents are utilized primarily to effect a dispersion between the aqueous and non-aqueous miscible components as well as to achieve a homogeneity with the component agents that are contained in the insoluble alginate compositions.

These surface active agents are also utilized in order to improve the wetting of a medical dressing or bandage in the event that a wound may be exudating, and the enhanced wicking in such a bandage or medical dressing serves to quickly absorb any blood or serum from a wound into the dressing. Other surface active agents, such as the Na salt of dodecyl $SO_4$ (sodium lauryl sulfate) or a member of the group of Tweens: Tween 20, polyoxyethylene sorbitan monolaurate; Tween 40, polyoxyethylene sorbitan monopalmitate, or Tween 85, polyoxyethylene sorbitan trioleate may be incorporated into the alginate composition without deviating from the novelty of the invention described herein.

Not that in the examples cited herein, the effervescent compound that reacts with the water soluble dilute acetic acid with the resultant evolution of a gas which becomes entrapped in the formation of the gel foam network is sodium bicarbonate. Other water soluble effervescent compounds may be utilized and other acids may be utilized to produce the evolution of gases, which become entrapped in the alginate gel composition without deviating from the novelty of the invention described herein. Thus, various water insoluble metal salts that can react with water soluble acids are calcium carbonate, calcium phosphare dibasic, barium carbonate, or zinc carbonate. Examples of suitable acids would include acetic acid, lactic acid, maleic acid, gluconic acid, and ascorbic acids.

Should it be desirable to utilize gases other than carbon dioxide to form the foam that forms the stable hydrogel composition described herein, inert gases such as nitrogen or argon, or other gases may be directly introduced into the alginate composition described in the claims herein as long as the alginate compositions described have a viscosity greater than the buoyance of the gases entrapped therein. The addition of such other gases will cause the formation of a stable hydrogel silver alginate foam composition in accord with the novelty of the invention described herein.

Example 4 described above incorporates a maltodextrin chemical within the alginate foam composition have a dextrose equivalent of 13.0–17.0. It is clear that other maltodextrins having dextrose equivalents other than 13.0–17.0 such as those which are available having dextrose equivalents of 4.0–7.0 and 16.5–19.5, may be utilized within the scope of the invention described herein without deviating from the novelty of the invention herein described.

Note that in Example 8, we introduce a highly hydrophilic chemical called "DriMop" (sodium polyacrylate polymer) for the purpose of enhancing the moisture-absorbing capacity of the dressing. Other hydrophilic compounds may be utilized in order to achieve enhanced moisture-absorbing capacity of the dressing. Other hydrophilic compounds may be utilized in order to achieve an enhanced moisture absorption of the dressing without deviating from the novelty of the invention described herein.

The pH of the silver alginate foam composition as well as the silver alginate-calcium alginate foam composition described herein may vary over a relatively wide range of pH due to the stability of these alginate compounds. However, the pH of the final compositions utilized may be altered commensurate with the use of these preparations in medical dressings or implants and commensurate with the specific characteristics of chemical agents and/or medicaments that are added to the silver alginate and calcium alginate compositions whose stability may be impaired by too acid or too alkaline a pH.

I claim:

1. A process for making an aqueous insoluble silver alginate sponge or foam product to be utilized in the preparation of wound dressings comprising the steps of:
   (I) making an aqueous solution of a water soluable alginate composition;
   (II) while allowing the total composition of (I) to be mixed, adding an aqueous-soluble silver salt capable of complexing with an aliquot of the soluble alginate to form an aqueous insoluble silver alginate product,
   (III) adding into the mixture (II) gaseous foam-forming or effervescent compound(s) and an acid to reset with the, effervescent compound,
   (IV) pouring said composite mixture onto a surface that will permit the evaporation of water so resulting in a sheet of a foam silver alginate composition.

2. The process of claim 1 wherein said water-soluble alginate is selected from a group consisting of ammonium, magnesium, potassium, and sodium slats of alginate or mixtures thereof.

3. The process of claim 1 wherein said aqueous soluble silver salt is silver nitrate.

4. The process of claim 1 wherein said foam is produced by an effervescent compound and an aqueous soluble acid which reacts with the effervescent compound.

5. The process of claim 4 wherein the said effervescent compound is selected from a group consisting of the alkali metal carbonates.

6. The process of claim 5 wherein said effervescent compound is sodium carbonate.

7. The process of claim 5 wherein said effervescent compound is sodium bicarbonate.

8. The process of claim 4 wherein said compound effervesces upon the addition of a water-soluble acid.

9. The process of claim 8 wherein said water-soluble acid is selected from the group is selected from the group consisting of acetic, lactic, malic, gluconic, hydrochloric, and ascorbic acids.

10. The process of claim 1 wherein a medicament is added to the silver alginate foam composition.

11. The process of claim 10 wherein said medicament is selected from the group consisting of collagen, maltodextrin, antibiotics, antibacterial agents, anti-inflammatory agents, ascorbic acid, amino acids, and mixtures thereof.

12. The process of claim 1 wherein a plasticizer is added to the silver alginate foam compositions.

13. The process of claim 12 wherein said plasticizer is selected from a group consisting of glycerin, propylene glycol, ethylene glycol, polyethylene glycol or mixtures thereof.

14. The process of claim 1 wherein a surface-active agent is added to the silver alginate foam compositions.

15. The process of claim 14 wherein said surface active agent is selected from a group consisting of polyoxyethylene sorbitan monolaurate, polyoxyethylene sorbitan monopalmitate, polyoxyethylene sorbitan monooleate, polyoxyethylene sorbitan trioleate, polyoxyethylene-polyoxypropylene block polymer, or a mixture thereof.

16. The process of claim 1 wherein the surface onto which the composite mixture is poured is a fibrous cloth.

17. The process of claim 16 wherein said fibrous cloth is selected from cloths prepared from cotton, polyester, wool, nylon, rayon, or mixtures thereof.

18. The process of claim 5 wherein said effervescent compound is calcium carbonate.

19. The process of claim 18 wherein said compound effervesces upon the addition of a water-soluble acid.

20. The process of claim 19 wherein said water-soluble acid is hydrochloric acid.

21. The process of claim 20 wherein the calcium chloride formed by the reaction of calcium carbonate and hydrochloric acid results in the complexing of the calcium ion of the calcium chloride with the residual of the soluble alginate to form an aqueous insoluble calcium alginate product.

22. The process of claim 21, wherein a medicament is added to the silver alginate calcium alginate position.

23. The process of claim 22 wherein said medicament is selected from the group consisting of collagen, maltodextrin, antibiotics, antibacterial agents, anti-inflammatory agent, ascorbic acid, amino adds, and mixtures thereof.

24. The process of claim 21 wherein a plasticizer is added to the silver alginate-calcium alginate foam composition.

25. The process of claim 24 wherein said plasticizer selected from a group consisting of glycerin, propylene glycol, ethylene glycol, polyethylene glycol or mixtures thereof.

26. The process of claim 21 wherein a surface-active agent is added to the silver alginate-calcium alginate foam composition.

27. The process of claim 26 wherein said surface-active agent is selected from a group consisting of polyoxyethylene sorbitan monolaurate, polyoxyethylene sorbitan monopalmitate, polyoxyethylene sorbitan monooleate, polyoxyethylene sorbitan trioleate, polyoxyethylene-polyoxypropylene block polymer, or a mixture thereof.

28. The process of claim 21 wherein the composite mixture containing a cross-linked foam composition of silver alginate and calcium alginate is poured onto a surface that will permit the evaporation of water so resulting in a sheet of a foam silver alginate-calcium alginate composition.

29. The process of claim 28 wherein said fibrous cloth is selected from cloths prepared from cotton, polyester, wool, nylon, rayon, or mixtures thereof.

30. A silver alginate-calcium alginate cross-linked foam composition produced by the process of claim 21.

* * * * *